United States Patent [19]

Saccocio

[11] Patent Number: 5,306,641
[45] Date of Patent: Apr. 26, 1994

[54] APPARATUS AND METHOD FOR DETERMINING GEL RATE OF POLYMERIZABLE COMPOSITIONS

[76] Inventor: Edward J. Saccocio, 1790 Sugar Run Trail, Bellbrook, Ohio 45305

[21] Appl. No.: 746,068

[22] Filed: Aug. 12, 1991

Related U.S. Application Data

[63] Continuation of Ser. No. 558,587, Jul. 27, 1990, abandoned.

[51] Int. Cl.$^5$ .............................................. G01N 33/44
[52] U.S. Cl. ........................................ 436/85; 436/34; 436/50; 436/181; 422/131; 422/133; 422/135; 422/186.3; 356/426; 356/427; 73/64.43
[58] Field of Search ............... 436/85, 34, 50, 181; 422/131, 133, 135, 186, 186.3; 356/426, 427; 250/573; 366/106, 101, 212, 240, 332; 522/13; 73/64.1

[56] References Cited

U.S. PATENT DOCUMENTS

| | | | |
|---|---|---|---|
| 3,544,074 | 12/1970 | Karpacheva | 366/106 |
| 3,767,535 | 10/1973 | Havewala et al. | 366/332 |
| 3,830,969 | 8/1974 | Hofstein | 356/427 |
| 3,989,383 | 11/1976 | Paulson | 436/34 |
| 4,038,037 | 7/1977 | Wilmsen | 422/133 |
| 4,211,751 | 8/1980 | Keggenhoff et al. | 422/135 |
| 4,398,894 | 8/1983 | Yamamoto | 73/64.1 |
| 4,740,460 | 4/1988 | Sakata et al. | 73/64.1 |

OTHER PUBLICATIONS

Perkin Elmer Corporation: Thermal Analysis User Newsletter (Feb. 1990).
Perkin Elmer Corporation: Thermal Analysis DPA7 (Oct. 1988).
Perkin Elmer Corporation: DMA Dynamic Mechanical Analyzer (Feb. 1990).
Perkin Elmer Corporation: Price List (Jun. 1989).

*Primary Examiner*—Robert J. Warden
*Assistant Examiner*—Laura E. Collins
*Attorney, Agent, or Firm*—R. M. Saccocio

[57] ABSTRACT

Apparatus and methods for accurately determining the gel time of oxygen inhibited polymerizable compositions is provided. Gel times in these compositions are related to dissolved oxygen concentration. The inventive method and apparatus use a small diameter capillary tube filled with the composition and sealed thereafter at one end to include an air space between the end of the liquid column and the sealed end of the tube. A pulsed force of air is applied to the unsealed end of the tube which causes the column of liquid and air/liquid interface to move in accordance with the amplitude of the pulsed air force. A motion detector sensor is located at the air/liquid interface. A light source is then applied to the polymerizable column within the tube causing it to gel. Recording equipment appropriately connected to the motion detector sensor visually describes the motion of the air/liquid interface which becomes zero at the gel point. A method to determine the gel time of a thermally initiated polymerizable material is disclosed which involves the addition of a photoinitiator to the composition and determining the curing time using the photoinitiator material.

12 Claims, 2 Drawing Sheets

APPARATUS AND METHOD FOR DETERMINING GEL RATE OF POLYMERIZABLE COMPOSITIONS

This application is a continuation, of application Ser. No. 07/558,587, filed Jul. 27, 1990, now abandoned.

BACKGROUND OF THE INVENTION

1. Field of the Invention

This invention pertains in general to the field of polymerizable compositions which are curable by various energy sources and in particular to apparatus and methods for determining gel time, initiator half-lives, and oxygen concentrations for prepolymer fluids commonly known as monomers.

2. Description of the Prior Art

In general, a class of materials have been developed through organic chemistry, known as monomers which exist as fluid at ambient temperatures but when cured, are changed into a hard, solid substance known as polymer. Two major characteristics of polymers are that they form a thin and hard coating and that they tenaciously adhere to a substrate surface. Again, in general, certain monomers may be combined with a cure preventing inhibitor, such as oxygen and a chemical reaction initiator such as borate. There are other inhibitors and many other initiators. The oxygen inhibitor maintains the monomer in a fluid state; accordingly, upon the depletion of oxygen, the initiator converts the monomer into a polymer. The initiator, among other things, determines the particular type of energy which may be used to cure the monomer. For example, monomers may be cured by heat, white light, ultraviolet light, radiation electron beam, and laser energy sources. Borate is generally light curable and is also sensitive to heat but to a lesser degree.

The tenacious adhering and hardness properties of polymers have relatively recently found commercial acceptance in the field of thin coatings applied onto a base material. Thus, in the past, the surface coating of such items as beverage cans and printing of paper boxes and magazines were previously accomplished by the use of paints or inks which dried in either heated or ambient air conditions. These traditional coatings have been substantially replaced by polymerizable coatings which are curable by one or more of the above-mentioned energy sources. For example, industry now routinely uses curable lacquer, curable acrylic, curable ink, curable wood finishes, and even curable adhesives made from monomers in place of the previous traditionally dried compositions. In these applications, a polymerizable composition comprising a monomer and the basic product is mixed with an initiator which, during an induction period of exposure to an energy source, removes oxygen within the composition and thereafter polymerizes the coating into a very hard, long-lasting thin film. The initiator within the polymerizable composition results in the rapid curing of the composition when acted upon by means to which the initiator is sensitive.

This recent use of fast-curing compositions for thin coating applications has resulted in numerous advantages. For example, extremely fast production line speeds are achieved. More flexibility and less waste are achieved. In general, the technique is non-polluting, which eliminates discharge problems, expensive air cleaning, and results in better plant conditions. Multi-color printing is made much easier and cheaper. The finished product achieves a much higher quality, a better appearance and finish, and performs better. Understandably, the coating of products by polymerization has achieved widespread acceptance by many industries in a myriad of different fields.

The use of monomers or polymeric compositions is not limited to the field of thin coatings. Polymerization is, for example, used to manufacture rubber tires. In this field, a thermal initiator is used such that when the liquid material fills the tire mold, the application of heat turns the liquid into solid rubber in accordance with the gel time of the polymerizable composition.

In the class of monomers which are oxygen inhibited, the oxygen determined-induction exposure time sets the lower limit for curing time since this is the exposure time required by an energy source (to consume the oxygen within the polymerizable composition) before any polymer chemistry can begin. That is, the induction time sets the minimum exposure time required in a curing operation. As such, oxygen is a natural inhibitor to free radical polymerization chemistry and represents expended energy before curing can take place. Oxygen is likewise a principal stabilizer in free radical systems (polymerizable compositions) and is necessary for storage, processability, and shipability of the same.

Over the years, different techniques have been developed in order to determine the gel time (the time required to initiate cure in a monomer) for variously-initiated polymerizable compositions under reproducible conditions. Among these, one prior art method involves the use of an infra-red energy. This technique utilizes the change in absorbance corresponding to the disappearance of the carbon-carbon double bonds on photoinitiated polymerization and deals more with the state of cure rather than the gel point beginning of cure. Another prior art method uses the contraction of the photocuring formulation. In this technique, an interface between water and the photoinitiated formulation forms part of a capacitor. The change in capacitance of the arrangement is directly proportional to the position of the air-water interface. Thus, measuring the time involved with the change in capacitance, determines the curing time of the composition.

Still other techniques for determining the gel time or curing time of polymerizable compositions comprise a differential scanning calorimetry method, a pulsed NMR method, and a photoacoustic spectroscopy method.

A prior art commercially available system for the study of photoinitiated polymerizations comprises the Perkin-Elmer DPA7 double beam photo-calorimetric accessory. This apparatus permits the laboratory investigation of the effects of ultraviolet light on a wide variety of materials. Photo-calorimetry provides a means for monitoring of the curing process and the evaluation of the effects of temperature, different ultraviolet wavelengths, influence of atmosphere, and the varying amounts and types of photoinitiators. This apparatus uses a differential scanning calorie meter measuring the amount of energy absorbed or released from a sample with the temperature being precisely controlled. Thus, the Perkin-Elmer apparatus measures energy changes resulting from temperature-induced reactions.

In general, the above-described apparatus and methods are too sophisticated or too complex to be used for production-related control functions, and, in general, are not so used. One such production-related use is to ensure the consistency of reactivity (gel time) of supplied polymerizable formulations. That is, whether the supplied raw materials will perform within a given set of predetermined specifications as compared to the polymerizable composition used to establish a pilot manufacturing sequence.

Repeatability of cure times is an important manufacturing parameter. It assures that a manufacturing sequence following the application of a surface coating does not begin too soon or too late. If it begins too soon, the polymer will not have sufficiently cured so that the finished coating is not acceptable. If the next manufacturing sequence occurs too late, the result is a loss of manufacturing time which decreases overall production and decreases efficiency.

Accordingly, a primary object of the present invention is to provide methods and apparatus for measuring the incipient gel time of a polymerizable composition which is repeatable and simple and directly associated with production line consistency.

Another object of the present invention is to provide simple methods and apparatus which can determine the gel time of polymerizable compositions regardless of the energy means or type, such as monochromatic light, white light, uv, heat, electron beam, catalytic, etc.

Another object of the present invention is to provide methods and apparatus for determining the gel time of polymerizable compositions which are simple, inexpensive, reliable, and consistently determine the gel time by a method which readily discerns the gel time.

Since inhibiting polymerizable compositions with oxygen comprises the most widely used inhibitor, direct knowledge of the rate of depletion of oxygen is important to be known. Similarly, direct knowledge of oxygen diffusion and oxygen stability are also important to be known.

Accordingly, another object of the present invention is to provide apparatus and methods which can determine the relative concentration of dissolved oxygen within oxygen-inhibited, polymerizable compositions.

Another object of the present invention is to provide methods and apparatus that can be used to determine oxygen diffusivity in oxygen-inhibited polymerizable compositions.

Yet another object of the present invention is to provide methods and apparatus that can be used to determine oxygen depletion rates in oxygen-inhibited polymerizable compositions.

Still another object of the present invention is to provide apparatus and methods that can be used to determine thermal initiator reactivities (half-lives) in thermally-initiated polymerizable compositions whereby the initiator exists not independently of but rather within the polymerizable composition.

The above-stated objects as well as other objects which, although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives, as well as others, as may be determined by a fair reading and interpretation of the entire specification, claims, and drawings herein. The present invention comprises apparatus and methods for determining the gel time, thermal initiator half-life, the concentration of dissolved oxygen, oxygen diffusivity, and oxygen depletion rates of polymerizable compositions.

A small diameter tube which is transparent to the energy source is filled with a polymerizable composition may be sealed at one end, leaving an air gap or space between the sealed end and the beginning of the liquid polymerizable composition. The other end of the small diameter tube is connected to a pulsed air supply which, when activated, causes back and forth movement of the liquid column and necessarily of the air-to-liquid interface within the tube at the sealed end thereof. The body of the tube in a small zone near its center is then exposed to an appropriate energy source consistent with the initiator within the polymerizable composition. A motion detector sensor is positioned at the air-to-liquid interface and connected to appropriate recording instrumentation such as a recording chart. Before the energy source is activated, the motion of the liquid column is shown on the recording chart and indicates consistent pulsed movement which appears as a sine wave. Activation of the energy source is then effectuated. After a period of time known as the gel time elapses, a plug is formed in the small zone where the exposure was made, constricting the motion of the entire liquid column and the recording instrument reflects the stoppage. Depending upon the speed of the recording chart and the amplitude of the pulsed movement of the liquid column, the onset of gelling and the completion of the same is readily determinable and viewable. The gel time thus obtained may then be directly related to the same polymerizable composition used in manufacturing procedures and thereby allow setting of the manufacturing time parameters and the quality control parameters.

A principle finding and unique part of the invention is that ultraviolet polymerizable compositions within a small diameter tube can be polymerized by focused white light. It has been determined that there exists tails to the sensitivity of ultraviolet initiators which extend into the wavelength reach of white light which are sufficient to produce gelation with reasonable exposure. Thus, the inventive apparatus and methods using white light may be used for any type of light-curable monomer.

Gel times have been demonstrated and are well known to correlate linearly with oxygen levels within oxygen inhibited compositions so that the gel point is a reflection of oxygen content under the measured conditions. Herein, then, is the basis of an in-solution measurement of a vital stability parameter, namely: oxygen, that has heretofore been virtually inaccessible.

The invention further comprises a method of indicating the time or speed with which an oxygen inhibited polymerizable composition loses one-half of its content. This is accomplished by determining the gel rate of the composition using the inventive apparatus.

The invention further involves the methods of determining the depletion time of an inhibitor such as oxygen from polymerizable compositions at different temperatures by placing a number of prepared glass tubes containing the same polymerizable composition in a bath or oven held at a constant temperature. Then, on a time-spaced and time-recorded basis, the samples are removed and tested for gel time, as above. The resulting data may, for example, be used to determine shelf life or even establish maximum processing time during manufacturing.

Another method of the invention involves determination of the amount of oxygen remaining in a thermally initiated polymerizable composition. This method adds an ultraviolet photosensitive initiator to the composition. The sample is then tested for gel time from which oxygen content may be determined. The determined amount of oxygen comprises the amount of oxygen remaining in the thermally initiated polymerizable composition. Simple subtraction reveals the amount of oxygen lost.

Still another method uses the inventive apparatus to measure the amount of oxygen gained by a polymerizable composition which contains a predetermined amount of oxygen less than the saturated percentage at ambient conditions. By testing for gel time, the actual oxygen concentration becomes known. The amount of oxygen gained is determined by a simple subtraction.

BRIEF DESCRIPTION OF THE DRAWINGS

Various other objects, advantages, and features of the invention will become apparent to those skilled in the art from the following discussion taken in conjunction with the following drawings, in which.

DESCRIPTION OF THE PREFERRED EMBODIMENTS

Figure 1:
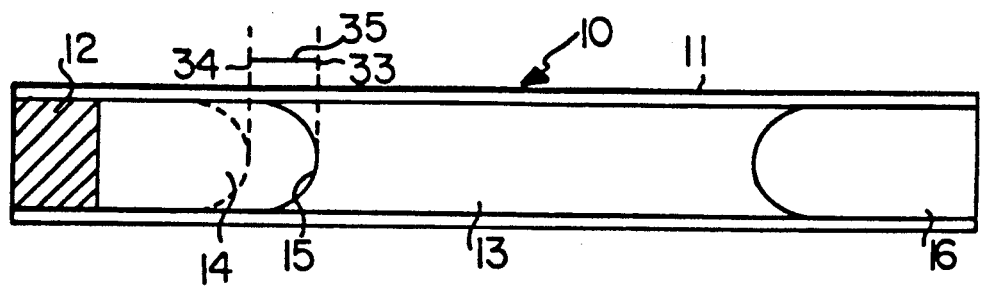
FIG. 1 is an enlarged plan view, in cross section, of a typical tube filled with a photocurable composition.

As required, detailed embodiments of the present invention are disclosed herein: however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings in general, wherein like characteristics and features of the present invention shown in the various FIGURES are designated by the same reference numerals.

Referring now in particular to FIG. 1, there is depicted therein a typical elongated tube which is filled with a particular light-curable liquid polymerizable composition whose gel time is desired to be determined. The tube arrangement 10 comprises an elongated, thin-walled, small-diameter tube 11 which is sealed at one end thereof 12 with, for example, a wax plug. The tube 11 is filled with a liquid polymerizable composition 13 leaving a column of air 14 between the sealed end 12 and the adjacent liquid column of liquid polymerizable composition 13 and thereby creating an air-liquid interface 15. For the sake of convenience, the phrase "liquid polymerizable composition" will hereafter at times be abbreviated to "liquid." The tube 11 is made from a material which is transparent to the particular energy source being used to cure the polymerizable composition contained therein. For example, when the polymerizable composition is light curable, ordinary glass may be used. The other end 16 of tube 11 is unsealed If the tube 11 is of sufficiently small diameter, for example, 0.005 inches in diameter, the liquid 13 will remain in position within tube 11 regardless of unsealed end 16. Since the liquid-filled tube arrangement 10 is, as above-stated, sensitive to or cured by light, it is a requirement that the tube 11 be filled with the liquid 13 under low-light or no-light conditions and maintained in such environment until the actual gel time is to be determined.

In laboratory tests, capillary glass tubes having an outer diameter ranging from 0.5 to 1.5 millimeters and a length from fifty to one hundred fifty millimeters have been found to work satisfactorily. Such tubes were filled with twenty-five to seventy-five millimeters of a polymerizable composition. Other sizes, materials, and amounts may also be used, providing the teachings provided herein are followed. Also, it is within the practice of this invention that end 12 is not sealed so long as the column of liquid 13 remains within tube 11 during the pulsing movement.

Figure 2:
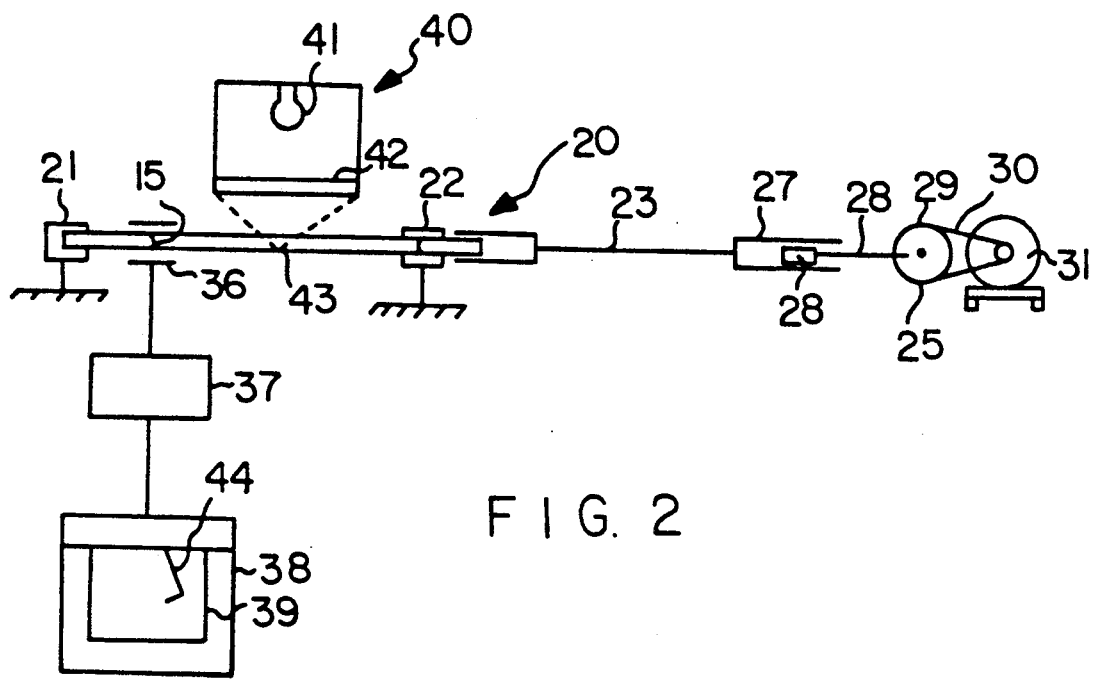
FIG. 2 is a schematic rendition of the apparatus used to determine the gel time of the monomer arranged in a tube as per FIG. 1.

FIG. 2 of the drawings illustrates a schematic view of the apparatus and methods to determine the gel time of the liquid 13 within tube 11. The liquid-filled tube arrangement 10 is supported within apparatus 20 at both of ends 12 and 16 by supports 21 and 22, respectively. Such support must leave unobstructed the liquid-air interface 15 and the open end 16 of tube 11. The open end 16 of tube 11 is connected with suitable flexible tubing 23 to a pulsed air supply arrangement 25 capable of approximately 0.5 to 5 psi at 2 to 10 Hz.

Pulsed air supply arrangement 25 may consist of a piston 26 fitted for axial motion within cylinder 27 and connected to a connecting rod 28 which, in turn, is connected to a fly wheel 29. Fly wheel 29 may be belt driven by belt 30 which connects fly wheel 29 to motor 31. Since a pulsed air force is desired to be placed on the column of liquid 13 within tube 11 such that the column of liquid 13 moves axially within tube 11 by compressing and uncompressing the small column of air 14 trapped between the column of liquid 13 and the sealed end 12 of tube 11, line 23 may be directly connected to cylinder 27 with no check valves or other equipment therebetween. In this manner the increased and decreased pressure created by piston 26 when moving within cylinder 27 applies a pulsed air source of force to the column of liquid 13 in tube 11. This, in turn, moves the air-liquid interface 15 back and forth a distance 35 between positions 33 and 34 (see FIG. 1).

Referring still to FIG. 2 of the drawings, the air-liquid interface 15 is positioned within the operating range of a motion detector sensor 36. Many types of motion detectors are available but a preferred sensor is one of the photo-interrupter type which is an integrated device comprising both an infrared light source and a photo detector, for example General Electric Model No. H21A3. Motion detector sensor 36 must be able to operate and sense the movement 35 of air-liquid interface 15. Sensor 36 is appropriately connected to a signal amplifier 37 which, in turn, is connected to an appropriate recording instrument 38, such as a pen chart which depicts the motion of air-liquid interface 15. It is preferable that recording device 38 have a movable chart associated therewith so that the relationship of the amplitude of motion of interface 15 with time be readily discernable.

A white light source 40, preferably u=tungsten-halogen, is focused onto the body of the liquid column 13 at its center such that a section approximately five millimeters long is exposed to the light source 40. A lens 42 may be used in connection with light bulb 41 so as to minimize heat and to intensify and direct the energy therefrom onto a particular point along the length of the column of liquid 13.

In utilizing the equipment arrangement shown schematically in FIG. 2 of the drawings, the following procedure may be used. A tube 12 is filled with a liquid 13 under no-light conditions; end 12 is sealed; the liquid-filled tube 11 is then assembled to supports 21 and 22. A flexible line 23 is connected to the unsealed end 16 of tube 11. A pulsed air source 25 is connected to flexible tube 23. Care is taken such that the air-liquid interface 15 is placed between the operating limits of motion sensor 36. Pulsed air source 25 is then turned on and thereby causes the liquid column 13 and its associated air-liquid interface 15 to move in a distance 35 between lines 33 and 34. Signal amplifier 37 and recording instrument 38 are then turned on. A chart 39 then moves along recording instrument 38. In the meantime, a pen 44 associated therewith moves back and forth in accordance with the motion of air-liquid interface 15. When it is determined that everything is properly operating, light source 40 is turned on. Motion detector sensor 36 continues to monitor the amplitude of motion of air-liquid interface 15. The effect of light source 40 is to cause the liquid 13 within tube 11 after a period of time, to begin to gel or solidify within tube 11. Shortly thereafter, the entire cross section of the liquid 13 within tube 11 at its center will have become gelled such that the pulsed air supply 25 no longer gives any amplitude of motion to interface 15. By reviewing the data associated with chart 39 of recording instrument 38, the gel time of the particular polymerizable composition 13 within tube 11 may be determined.

Figure 3:
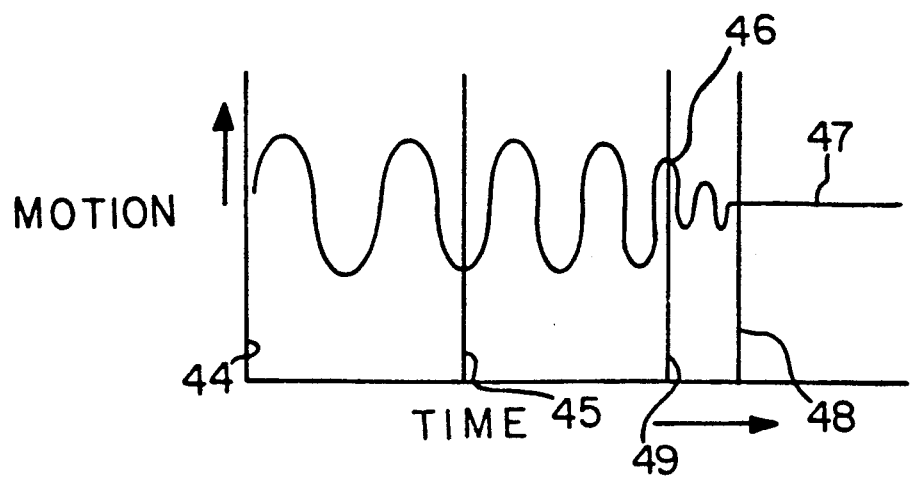
FIG. 3 comprises a typical graph indicating movement of an air-liquid interface versus time.

FIG. 3 characteristically depicts the amplitude of motion as registered by pen 44 in accordance with the motion of air-liquid interface 15. When the chart 39 is first turned on, the motion of interface 15 will reflect a constant cycling of the air-liquid interface 15 between a high and a low point equally about a common center. This event is shown in FIG. 3 as that part of the curve between vertical lines 44 and 45. The vertical line 45 indicates the time at which light source 40 is turned on. Thereafter, as the chart continues to move and the pulsed air supply source 25 applies its pulsed motion-causing movements to the column of liquid 13 within tube 11, the air-liquid interface 15 continues to equally move up and down as previously, until such time as the onset of gel point initiation occurs, which is shown at vertical line 49 in FIG. 3. At this time, it has been found that the diameter of the liquid 13 within tube 11 begins to decrease and the same amount of force applied by pulsed air supply 25 causes a lesser amount of motion of air-liquid interface 15. Then, as the liquid 13 continues to polymerize, the amplitude of motion of interface 15 becomes less and less very rapidly until such time as the entire cross-sectional diameter of liquid 13 has solidified and, therefore, no further motion of interface 15 occurs. This appears as the straight horizontal line 47 in FIG. 3 of the drawings. The time line 48 at which the total gelling of liquid 13 has occurred, is also shown in FIG. 3 of the drawings. The difference between time lines 44 and 48 determine the total gel time of polymerizable comprising liquid 13. The time between lines 48 and 49 represents the time from the initiation of gelling to the completion of the same.

The use of the inventive method and apparatus as described above will now be described in relation to various oxygen level determinations as regards those polymerizable compositions utilizing oxygen as an inhibitor.

Figure 4:
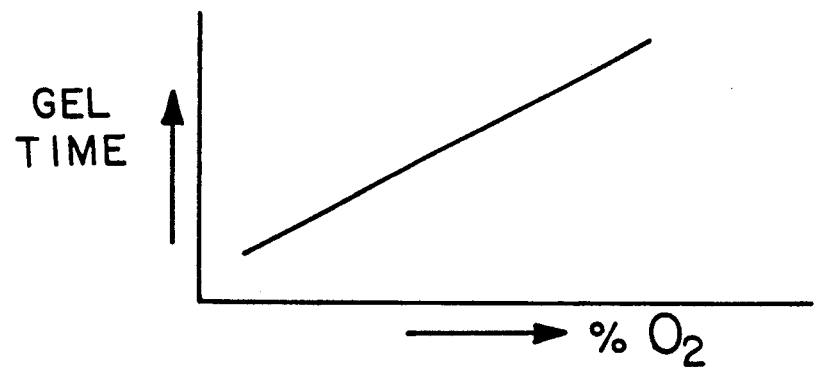
FIG. 4 comprises a typical curve of gel time versus percentage of oxygen in an oxygen inhibited polymerizable composition.
Figure 5:
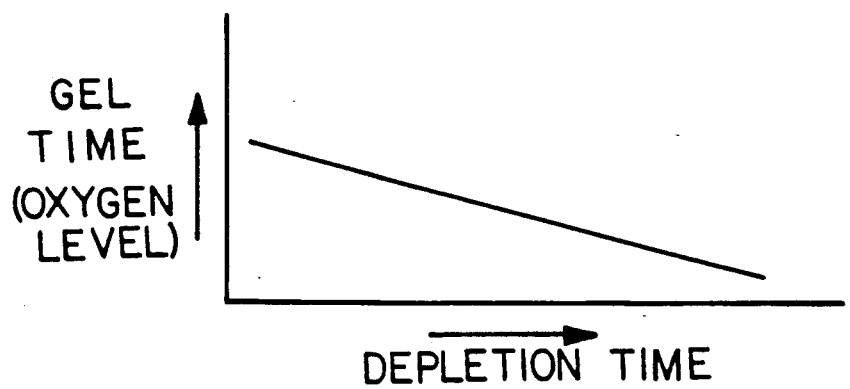
FIG. 5 comprises a typical curve of gel time versus depletion time at a single constant temperature in an oxygen inhibited polymerizable composition; and, FIG. 6 comprises a typical curve of gel time versus depletion time at a plurality of constant temperatures in an oxygen inhibited polymerizable composition.

For any given oxygen-inhibited polymerizable composition, it is known that the gel time of the polymerizable composition varies linearly with respect to oxygen level (See FIG. 4). Hence, for a given oxygen-inhibited polymerizable material, a gel time test may be conducted from a sample of the polymerizable material at a given time after formulation while at a given temperature. From this test, a first oxygen level for a particular time period may be determined. Then, after a predetermined period of time such as a week, two weeks, etc., passes, another sample of the given polymerizable material is tested for gel time. Of course, during this interval of time, the polymerizable material was maintained at a constant temperature in a closed container. From the second test, another oxygen level determination at a particular time may be determined. If desired, after another period of time elapses, a third test may be run from which another oxygen level determination at a particular time may be determined. From this data a curve, such as that shown in FIG. 5 of the drawings, may be plotted. In accordance with FIG. 5, it is seen that the oxygen level is continuously decreasing along a straight line with the passage of time. From this curve the shelf life or stability of the oxygen-inhibited polymerizable material may be determined. Such data or information is, of course, very useful for a formulator or a user of the polymerizable material. For example, the formulator knows his sales volume of a particular material and makes only that much such that all of it is sold well before the shelf life has passed. For the user, since he usually knows how much he uses of the material over a period of time, he need only order that much so that it is all used up before the end of the determined shelf life.

Figure 6:
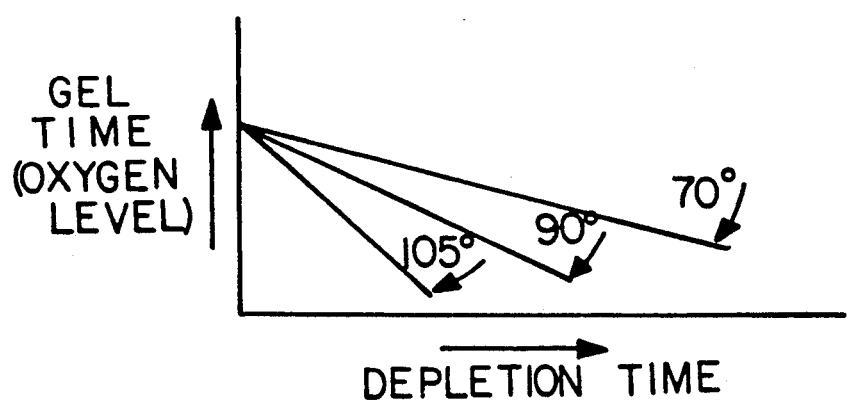

Somewhat similar to the determination made for oxygen stability above, a further curve, such as that depicted in FIG. 6 of the drawings, may be constructed by determining the oxygen level within a polymerizable material as it is depleted over a period of time while being maintained at constant but at different temperatures. The curve shown in FIG. 6 is characteristic of such a determination and graph construction. It is readily seen that the depletion time is much quicker for a polymerizable material maintained at a higher temperature as compared to a lower temperature. Such data would be very important to a user or even a formulator who might during processing maintain the polymerizable material at an elevated temperature. If such is the case, he may construct a curve such as that shown in FIG. 6 for the particular temperature he is interested in and from that determine the oxygen depletion time, which time would be factored into his processing to make certain that all of the oxygen is not depleted prior to that stage in the process where it is desired that polymerization occurs.

It may be desirable for a formulator or a user of polymerizable materials to know how much oxygen is depleted over a period of time at a given temperature. Such data may be obtained from a curve typical of that shown in FIG. 6 of the drawings, but developed for the particular polymerizable material in question. At the particular temperature in question, the difference in oxygen levels between any two periods of time comprises the amount of oxygen lost or depleted during that period of time. Such information may be useful, for example, where a particular process involving the polymerizable material or the inhibitor is being processed at an elevated temperature. By knowing the amount of oxygen lost at this temperature over a given period of time, the time parameters for the process in question may be set or may need to be changed.

Another determination which may be useful to inhibitor material manufacturers, polymerizable material manufacturers formulators of inhibited polymerizable materials, and users of the inhibited polymerizable materials may be determining the amount of oxygen that is gained by the composition during a particular process. Such gaining of oxygen having an oxygen content below the equilibrium point does, of course, occur in accordance with Henry's Law that the amount of gas that diffuses into a solution or liquid below the gas is dependent upon the concentration or amount of that gas over the liquid. Hence, for an oxygen inhibited polymerizable material, if the amount of oxygen therewithin is below the equilibrium point, the amount of oxygen within the atmosphere above the liquid will cause oxygen to diffuse into the polymerizable material. In order to determine the amount of oxygen thus gained, a gel point determination test of the polymerizable material at that particular time within the process may be made as described above. From this data when correlated to the previously known amount of oxygen within the polymerizable material, can be determined the amount of oxygen gained.

Yet another and very important determination or method in accordance with the present invention is to determine directly the rate of oxygen consumption in a thermally initiated polymerizable material at specified temperatures of interest. Traditionally, a manufacturer of thermal initiator materials specifies the half life of the material in various solvents as a parameter which helps determine for the user the cure time (the term "cure time" is being used for thermal gelation as distinguished from the term "gel time" which is used for photo gelation) for various polymerizable compositions using the thermal initiator. The half-life usually is stated in a time term where the initiator loses half of its initial mass during that time. From this data, a formulator or user than attempts to match a particular thermal initiator with the polymerizable material and anticipated time of polymerization during manufacture to select a desirable combination of thermal initiator and polymerizable material. Unfortunately, such half-life data is only indicative of the actual polymerization time. On the other hand, the inventive method described hereafter gives a formulator or user of polymerizable material a positive gauge which may be used to determine the cure time of a thermally initiated polymerizable material at any particular temperature desired. The inventive method contemplates adding an ultraviolet photoinitiator to a particular sample of a thermally initiated polymerizable material and placing a number of prepared tubes containing the new photo polymerizable composition into an oven at the intended cure temperature. Then, on a time-spaced and time-recorded basis, the samples are removed and tested for their photo gel time by such apparatus as the inventive apparatus 10 described above or by any other known method of determining photo gel time or any other conceivable method and apparatus used to determine photo gel time. The thermal initiator, as it works toward curing the composition, begins consuming the inhibiting oxygen at a constant rate so that as each sample is taken and tested for photo gel time, a constant decreasing gel time (similar to that shown in FIG. 5) is observed. Since the (decreasing) gel time is proportional to oxygen content, the measurement shows the rate of loss of oxygen content. In this manner, formulators of thermally initiated polymerizable material and users of thermally initiated polymerizable material need not guess based on a given "half-life" data to exactly know the thermal initiator polymerization material cure time. In this regard, the curves depicted in FIGS. 5 and 6 of the drawings, as well as determinations made in accordance therewith, may also be utilized in determining the actual cure time of the thermally initiated polymerizable material.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. Apparatus for use with a polymerizable composition comprising in combination:
   container means to be filled with a polymerizable composition for forming a liquid column therein and along a length thereof;
   reciprocating means for applying a reciprocating motion to said liquid column within said container means;
   gelling means for gelling said polymerizable composition within said container means;
   means for determining when said reciprocating motion of said liquid column stops due to gelation of the liquid column across a diameter thereof anywhere along the length of said liquid column.

2. The apparatus of claim 1, wherein said means for applying reciprocating motion to said liquid column comprises a pulsed energy source.

3. The apparatus of claim 2, wherein said pulsed energy source comprises air compressed between a first pressure and a second pressure being applied to the liquid column within said container means.

4. The apparatus of claim 1, wherein said gelling means comprises a white light source.

5. The apparatus of claim 1, wherein said gelling means comprises an ultraviolet light source.

6. The apparatus of claim 1, wherein said gelling means comprises a monochromatic light source.

7. The apparatus of claim 1, wherein said gelling means comprises a heat source.

8. The apparatus of claim 1, wherein said gelling means comprises an electron beam source.

9. The apparatus of claim 1, wherein said gelling means comprises a catalytic hardener.

10. The apparatus of claim 1, wherein said container means comprises a tube.

11. The apparatus of claim 1, wherein said container means is closed at one end with an air pocket between the closed end and the liquid column and open at a second end with said open end being filled with a column of air, said column of air being fluid connected to said reciprocating means.

12. A method for determining the gel time of a polymerizable composition comprising the steps of:

placing a polymerizable composition within a container forming a liquid column;

subjecting said liquid column to axial reciprocating motion within said container;

applying a motion sensor to said liquid column;

applying a polymerizing means to said liquid column thereby causing gelation and causing stoppage of said reciprocating motion of said liquid column; and determining gel time by noting the difference in time between initiation of polymerization and the stopping of reciprocating motion.

* * * * *